(12) United States Patent
Lee, Jr.

(10) Patent No.: US 7,044,955 B2
(45) Date of Patent: May 16, 2006

(54) REMOVABLE CARTRIDGE FOR A MICRODERMABRASION UNIT

(75) Inventor: John B. Lee, Jr., Ridgefield, CT (US)

(73) Assignee: Focus Medical, LLC, Bethel, CT (US)

( * ) Notice: Subject to any disclaimer, the term of this patent is extended or adjusted under 35 U.S.C. 154(b) by 148 days.

(21) Appl. No.: 10/445,756

(22) Filed: May 27, 2003

(65) Prior Publication Data

US 2004/0243149 A1    Dec. 2, 2004

(51) Int. Cl.
*A61B 17/50*    (2006.01)

(52) U.S. Cl. .................. 606/131; 211/85.18; 248/310; 451/87

(58) Field of Classification Search ............... 606/131; 29/438; 451/39
See application file for complete search history.

(56) References Cited

U.S. PATENT DOCUMENTS

| | | | |
|---|---|---|---|
| 5,100,412 A * | 3/1992 | Rosso | 606/131 |
| 6,183,483 B1 * | 2/2001 | Chang | 606/131 |
| 6,235,039 B1 * | 5/2001 | Parkin et al. | 606/131 |
| 6,527,783 B1 | 3/2003 | Ignon | |
| 6,540,757 B1 * | 4/2003 | Hruska et al. | 606/131 |
| 2001/0023351 A1 * | 9/2001 | Eilers et al. | 606/131 |
| 2002/0151908 A1 * | 10/2002 | Mallett et al. | 606/131 |
| 2002/0169461 A1 * | 11/2002 | Simon et al. | 606/131 |

* cited by examiner

*Primary Examiner*—Corrine McDermott
*Assistant Examiner*—Christopher Prone
(74) *Attorney, Agent, or Firm*—Buckley, Maschoff & Talwalkar LLC (57) ABSTRACT

A removable cartridge is provided for use with a microdermabrasion unit. According to some embodiments, the cartridge includes a crystal source portion and a crystal waste portion. Moreover, the removable cartridge is adapted to receive a transfer apparatus from a microdermabrasion unit, the transfer apparatus being adapted to transfer crystals from the removable cartridge to the microdermabrasion unit. In other embodiments, the removable cartridge includes (i) a crystal source portion, (ii) a crystal waste portion, and (iii) a re-sealable portion adapted to prevent crystals from leaving the removable cartridge when a transfer apparatus is not present.

14 Claims, 8 Drawing Sheets

REMOVABLE CARTRIDGE FOR A MICRODERMABRASION UNIT

FIELD

The present invention relates to microdermabrasion. In particular, some embodiments of the present invention relate to a removable cartridge for a microdermabrasion unit.

BACKGROUND

Microdermabrasion is a procedure that may be performed, for example, to exfoliate layers of a patient's skin. In some cases, microdermabrasion is used to alleviate a skin condition (e.g., acne scars) and/or or to reduce the appearance of wrinkles (e.g., through collagen regeneration). Moreover, blood containing oxygen and nutrients may be drawn to the surface to help feed and repair the patient's skin cells.

During the microdermabrasion procedure, crystals may be supplied from a first container. A vacuum air flow is then used to spray or apply the crystals onto the patient's skin in a uniform manner. The crystals, along with dead skin cells, are then deposited in a second container to be eventually discarded.

An operator will need to replace or re-fill the first container when it runs out of crystals. Similarly, the operator will need to replace or empty the second container when it becomes filled with used crystals. Often, the operator will find it time consuming and inconvenient to perform these tasks—especially when the first container becomes empty (or the second container becomes full) while the microdermabrasion procedure is being performed on a patient. In addition, replacing, re-refilling and/or emptying the containers can be cumbersome (e.g., the container may be heavy and crystals may be spilled during the process).

In some devices, a pick-up tube with a small hole is provided within the first container. A vacuum air flow through the pick-up tube draws crystals into the hole to remove crystals from the first container. In this case, however, it can be difficult to adjust the rate at which crystals are drawn through the hole (e.g., to apply a weak or strong flow of crystals to the patient's skin).

Moreover, the crystals in the first container may become clogged (preventing the crystals from being drawn through the hole in the pick-up tube). In some devices, an operator can reverse the direction of a vacuum air flow to attempt to dislodge the clogged crystals. It can be difficult, however, to design a microdermabrasion device to reverse the vacuum air flow in an appropriate fashion (e.g., such that used crystals are not carried in the reversed vacuum air flow). In addition, the reversed vacuum air flow may not dislodge the crystals.

SUMMARY

To alleviate problems inherent in the prior art, some embodiments of the present invention introduce a removable cartridge having a crystal source portion and a crystal waste portion. The removable cartridge is adapted to receive a transfer apparatus from a microdermabrasion unit, the transfer apparatus being adapted to transfer crystals from the removable cartridge to the microdermabrasion unit.

According to other embodiments, the removable cartridge includes (i) a crystal source portion, (ii) a crystal waste portion, and (iii) a re-sealable portion adapted to prevent crystals from leaving the removable cartridge when a transfer apparatus is not present.

According to still other embodiments, a microdermabrasion unit includes a gravity drain to transfer crystals from a crystal source. Moreover, the unit includes a rotatable pick-up section having an opening through which crystals are drawn due to a vacuum air flow in the pick-up section, wherein rotation of the pick-up section varies a rate at which crystals are drawn though the opening.

With these and other advantages and features of the invention that will become hereinafter apparent, the invention may be more clearly understood by reference to the following detailed description of the invention, the appended claims, and the drawings attached herein.

DETAILED DESCRIPTION

Some embodiments described herein are directed to a microdermabrasion system to apply "crystals" to a patient's skin. As used herein, the term "crystals" can apply to any substance that is applied to a patients skin during a microdermabrasion procedure. By way of example only, the crystals may comprise aluminum oxide crystals and/or other appropriate substances.

Microdermabrasion System

Figure 1:
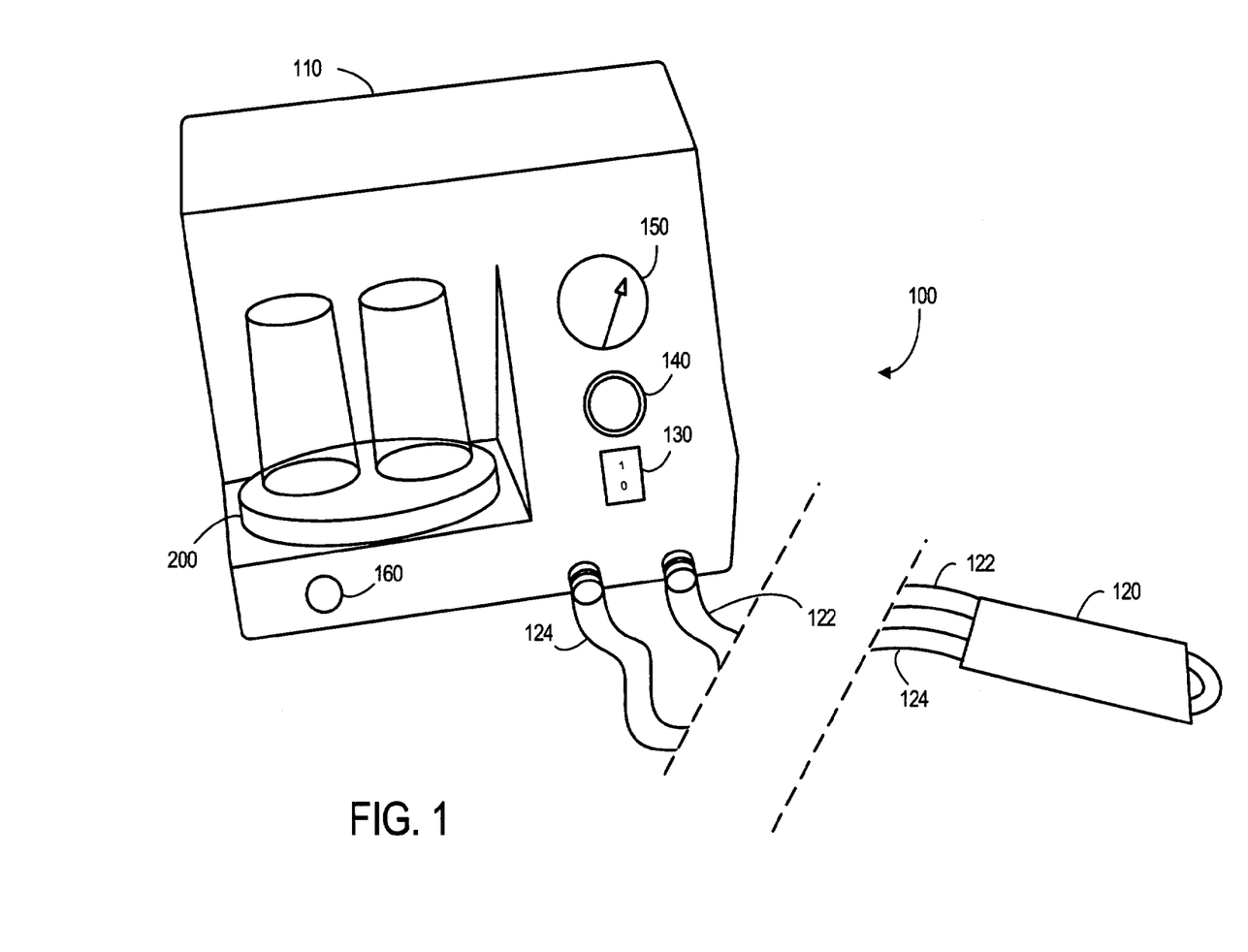
FIG. 1 illustrates a microdermabrasion system according to some embodiments.

As illustrated in FIG. 1, a microdermabrasion system 100 may include a microdermabrasion unit 110 coupled to a hand-piece 120. In particular, the microdermabrasion unit 110 may provide a vacuum air flow (containing crystals) to the hand-piece 120 via an output tube 122. An operator (e.g., a nurse or technician) may hold the hand-piece 120 and direct the air flow and crystals to a patient's skin. After striking the skin, the "used" crystals and skin cells return to the hand-piece 120 and are transferred back to the unit 110 via an input tube 124. The output and/or input tubes 122, 124 may comprise, for example, flexible plastic tubing with a ³⁄₁₆" inner diameter and a ⁵⁄₁₆" outer diameter.

The microdermabrasion unit 110 may also include an on/off control switch 130 (e.g., to apply or remove power to the unit 110). The microdermabrasion unit 110 may further include a vacuum adjustment control 140, such as a knob that can be rotated to change the pressure of the air flow. Similarly, a vacuum pressure gauge 150 may indicate the amount of pressure currently associated with the air flow. According to other embodiments, a digital vacuum pressure gauge may be provided.

A crystal flow control 160 may also be provided. The crystal flow control 160 may comprise, for example, a knob that can be rotated 90 degrees to change the amount of crystals contained in the air flow. One example of a crystal flow control 160 is described with respect to FIG. 6.

A "removable" cartridge 200 may be attached to the microdermabrasion unit 110 to supply crystals to the air flow and/or to store used crystals (and skin cells) for eventual removal. A used herein, the term "removable" means that the unit 110 and/or the cartridge 200 have been adapted such that the cartridge 200 can be removed and replaced by an operator. Some examples of removable cartridges 200 will now be described with respect to FIGS. 2 through 6.

Removable Cartridges

Figure 2:
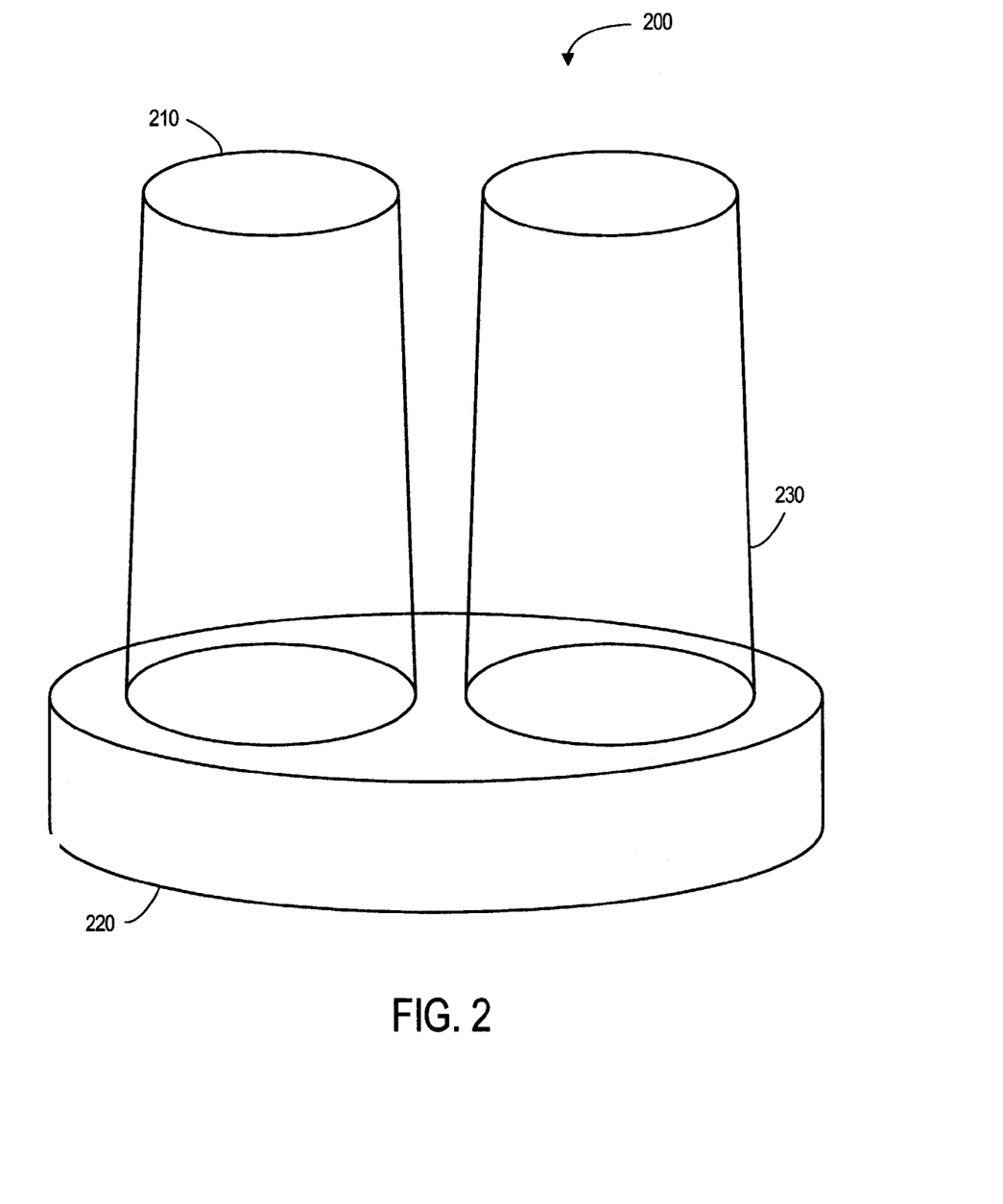
FIG. 2 illustrates a removable cartridge according to some embodiments.

FIG. 2 illustrates a removable cartridge 200 according to some embodiments. In particular, the removable cartridge 200 includes a crystal source portion 210 coupled to a base 220. The removable cartridge 200 also includes a crystal waste portion 230 coupled to the base 220. According to some embodiments the seals between the base 220 and the bottom rims of the crystal source portion 210 and crystal waste portion 230 are substantially air tight.

The crystal source portion 210 holds a supply of crystals that will be applied to a patient's skin during a microdermabrasion procedure and the crystal waste portion 230 holds used crystals and skin cells. That is, in a new cartridge 200 the crystal source portion 210 will be substantially full (with un-used crystals) and the crystal waste portion 230 will be substantially empty. After the microdermabrasion procedure is performed, the crystal source portion 210 will be substantially empty and the crystal waste portion 230 will be substantially full (with used crystals and skin cells). In this way, an operator can both replenish the crystal supply and discard used crystals and skin cells by replacing a single removable cartridge 200. According to some embodiments, the crystal source portion 210 and/or the crystal waste portion 230 are made using a transparent material, such as see-through plastic (e.g., to let an operator see how much crystal remains in the crystal source portion 210).

Figure 3:
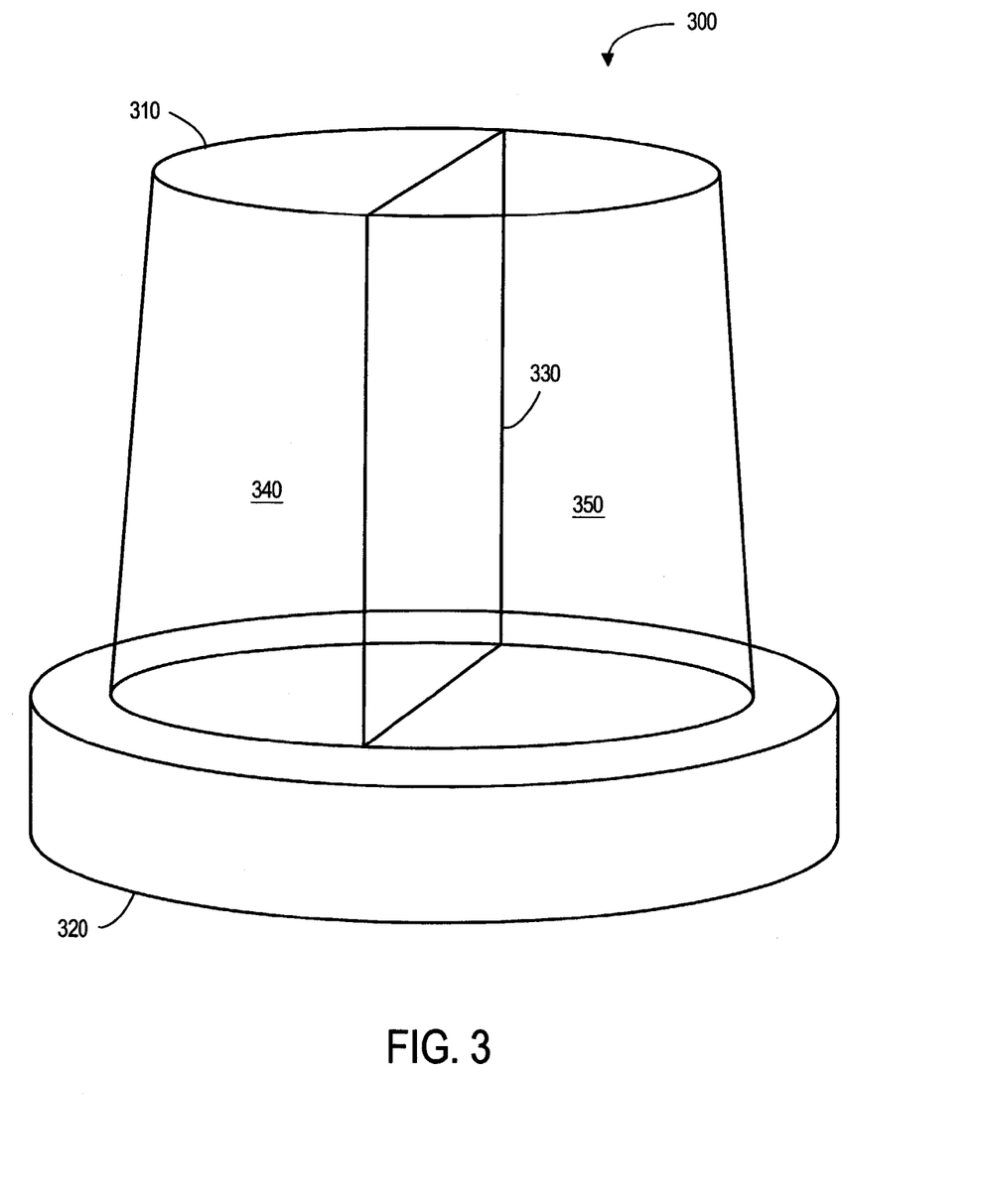
FIG. 3 illustrates another removable cartridge embodiment.
Figure 4:
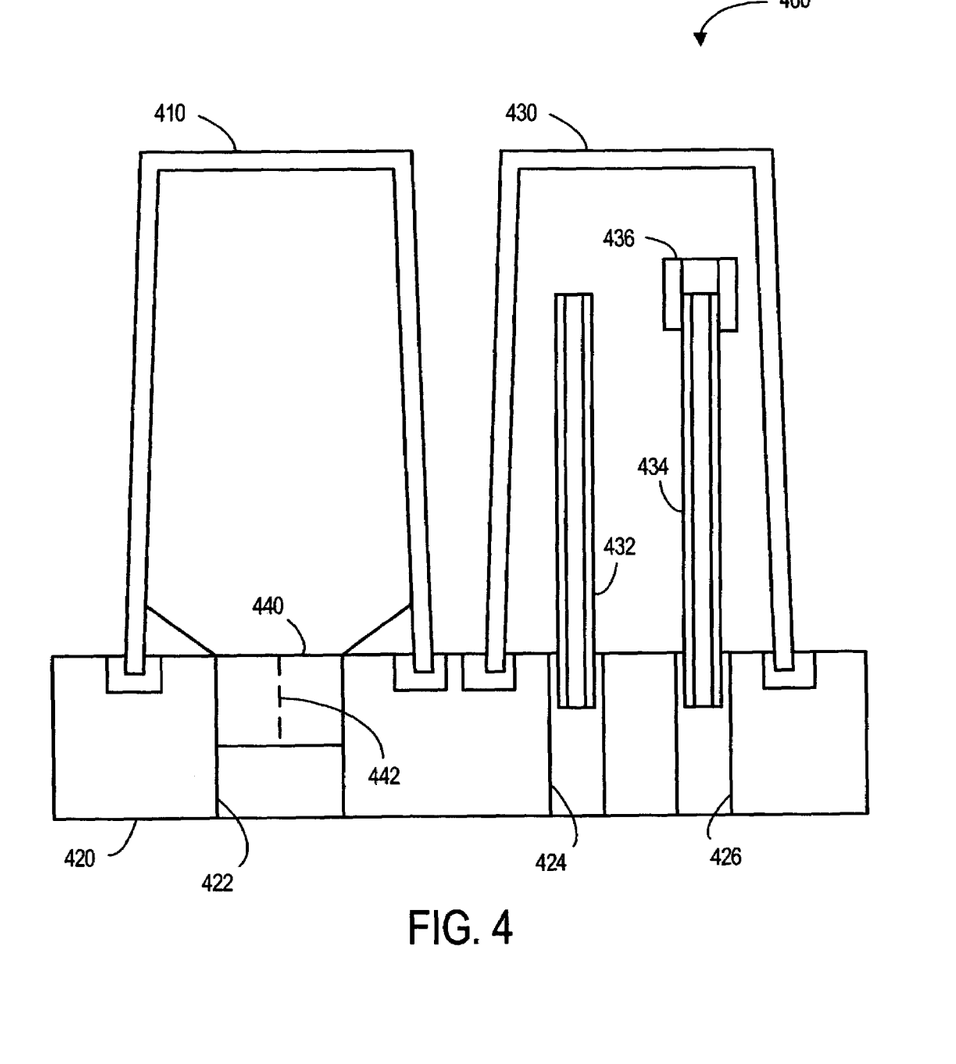
FIG. 4 is a cross-sectional view of a removable cartridge including a re-sealable portion according to some embodiments.

As described with respect to FIG. 4, the removable cartridge 200 may include a re-sealable portion. Moreover, as described with respect to FIGS. 4 through 6, the removable cartridge 200 may be adapted to receive a transfer apparatus (e.g., a portion of the microdermabrasion unit 110 that is adapted to transfer crystals from the removable cartridge 200 to the microdermabrasion unit 110). Although these features are described with respect to the removable cartridge 200 illustrated in FIG. 2, different cartridge designs may be used in accordance with any of the embodiments described herein. For example, FIG. 3 illustrates another design in which a removable cartridge 300 includes a single crystal portion 310 coupled to a base 320. A divider 330 separates the crystal portion 310 into a crystal source area 340 and a crystal waste area 350.

Removable Cartridges Having a Re-sealable Portion

FIG. 4 is a cross-sectional view of a removable cartridge 400 according to some embodiments. As before, the cartridge 400 includes a crystal source portion 410 coupled to a base 420 (to hold a supply of crystals) and a crystal waste portion 430 coupled to the base 420 (to hold used crystals).

In this case, the removable cartridge 400 also includes a re-sealable portion 440. As will be explained, the portion 440 is adapted to prevent crystals from leaving the removable cartridge 400 when a transfer apparatus (e.g., a tube from a microdermabrasion unit) is not present. The portion 440 is "re-sealable" in that it can be opened and closed more than once. Moreover, according to some embodiments, inserting a transfer apparatus into the removable cartridge 400 automatically opens the re-sealable portion 440.

By way of example, the re-sealable portion 440 might be foam unit (e.g., a disc-shaped unit) located inside a hole 422 in the base 420. The foam unit may have a slit 442 running though it's center (e.g., shaped as a line or an "x") such that a tube can be inserted through the slit 442. When no tube is present, the foam may expand so as to prevent crystals from leaving the crystal supply portion 410. According to some embodiments, the foam unit may further serve as a filter that permits a flow of air into the crystal source portion 410 (e.g., to facilitate a removal of crystals from the crystal supply portion 410 via a transfer apparatus).

According to some embodiments, the base 420 includes a waste inlet hole 424 and an air outlet hole 426. A waste inlet portion 432 (e.g., a tube) runs through the waste inlet hole 424 to receive used crystals. An air outlet portion 434 (e.g., a tube) runs through the air outlet hole 426 to allow air to flow out of the crystal waste portion 430. A filter 436 (e.g., a foam filter) associated with the air output portion may prevent used crystals from leaving the crystal waste portion 430.

Removable Cartridges Adapted to Receive a Transfer Apparatus

Figure 5:
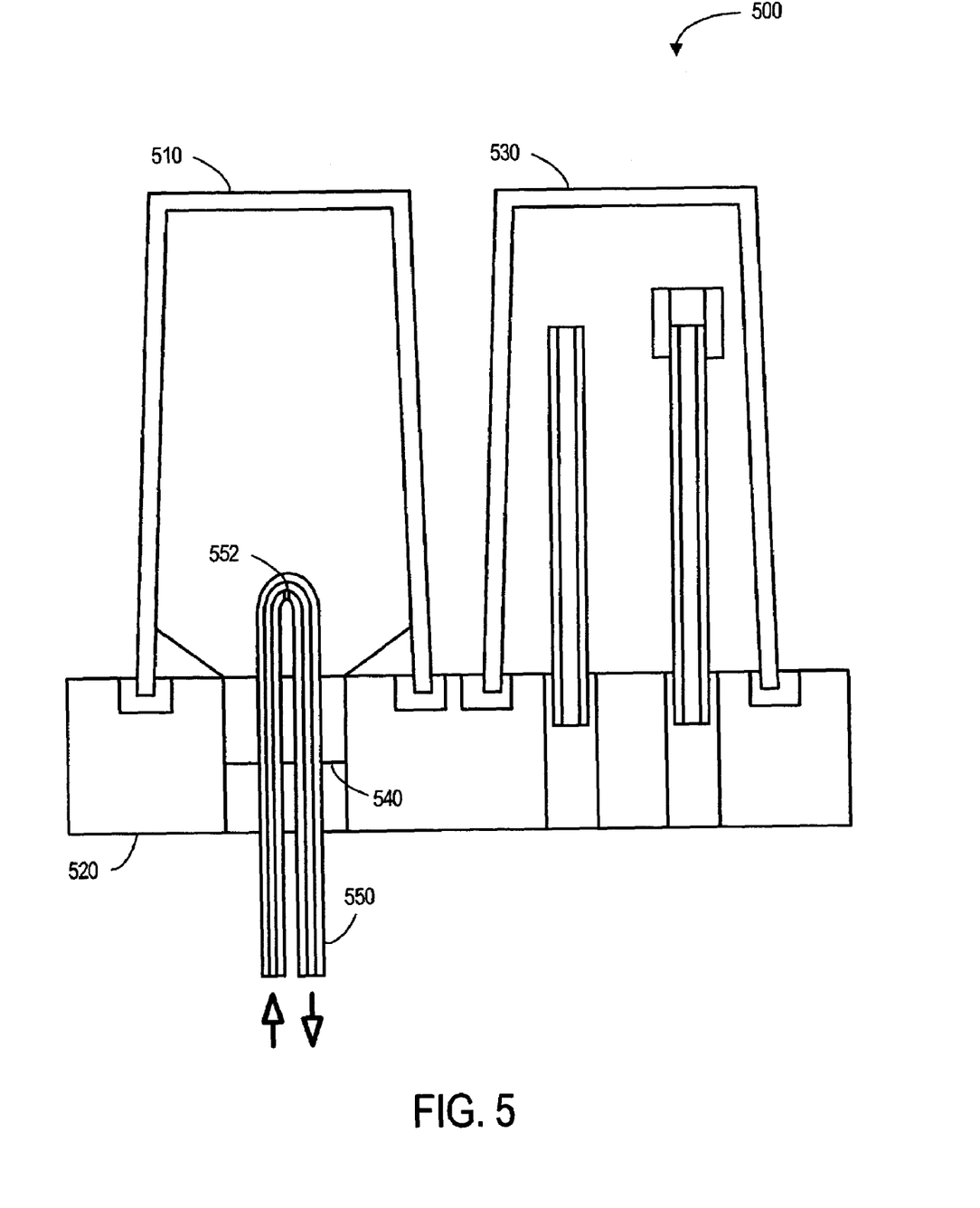
FIG. 5 is a cross-sectional view of a removable cartridge receiving a pick-up tube according to some embodiments.

FIG. 5 is a cross-sectional view of a removable cartridge 500 according to some embodiments. As before, the cartridge 500 includes a base 520 coupled to a crystal source portion 510 and a crystal waste portion 530. In this case, a transfer apparatus has been inserted into the removable cartridge 500. In particular, a pick-up section 550 having a vacuum air flow has been inserted into the crystal source portion 510. The pick-up section 550 may be, for example, a tube having an inverted U shape. The pick-up section 550 further includes an opening 552. As a result, a flow of air through the pick-up section 550 will draw an amount of crystal from the crystal source portion 510 through the opening 552 (e.g., so that the crystal can be applied to a patient's skin). In this example, a re-sealable portion 540 includes a slit that is co-planar with the cross-sectional view and that extends from the crystal source portion 510 to the bottom of the portion 540.

Figure 6:
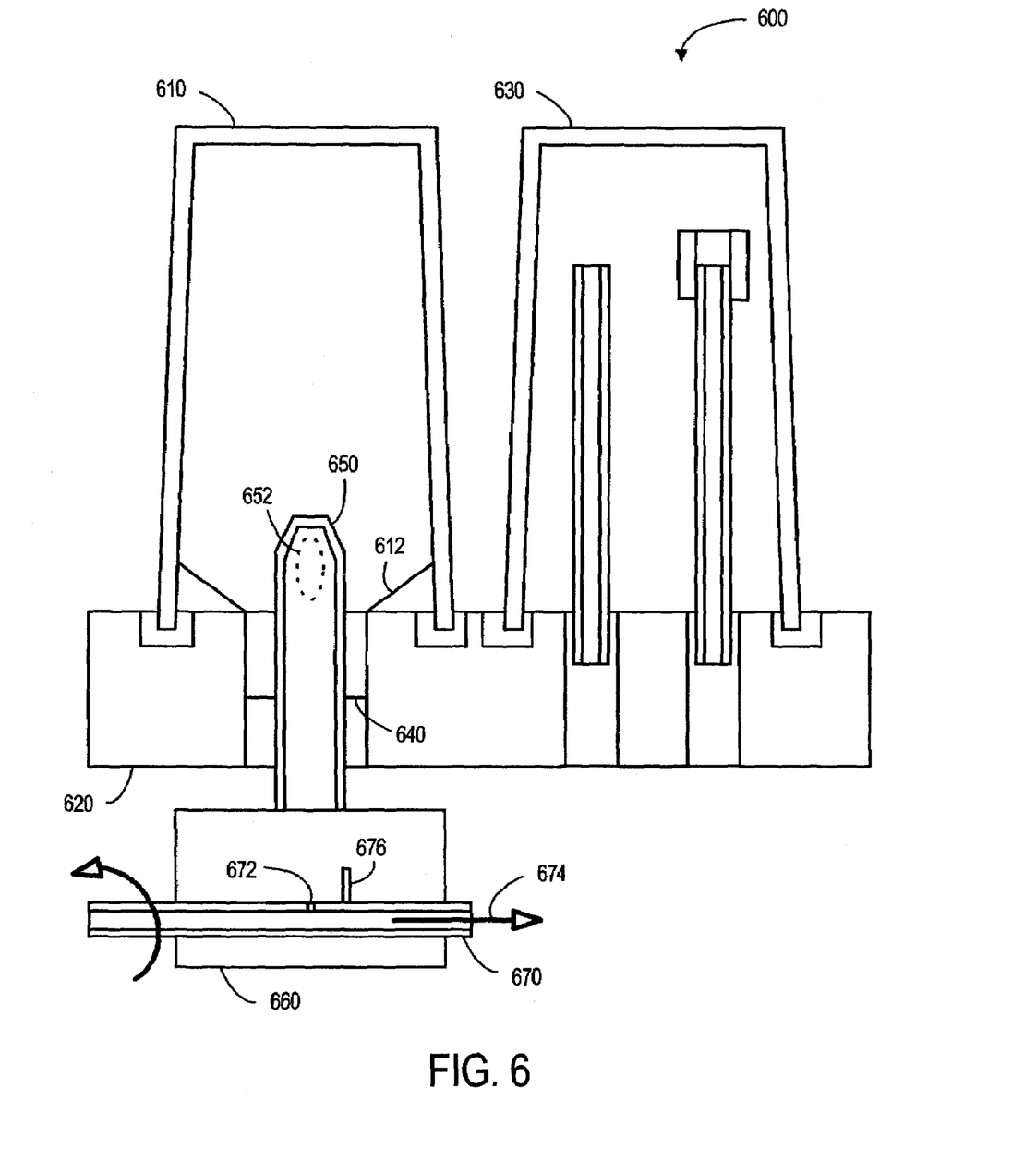
FIG. 6 is a cross-sectional view of a removable cartridge receiving a gravity drain according to another embodiment.

FIG. 6 is a cross-sectional view of a removable cartridge 600 according to another embodiment. As before, the cartridge 600 includes a base 620 coupled to a crystal source portion 610 and a crystal waste portion 630. In this case, the transfer apparatus received by the cartridge 600 through a re-sealable portion 640 is a gravity drain 650 (e.g., a tube) to transfer crystals from the crystal source portion 610. According to some embodiments, the bottom surface 612 of the crystal source portion 610 inclines from the sides of the crystal source portion 610 down to an opening that receives the gravity drain 650 to facilitate this transfer.

The gravity drain 650 transfers crystals through an opening 652 to a chamber 660. A pick-up section 670 (e.g., a metal tube) in the chamber 660 includes an opening 672 into which crystals are drawn when a vacuum air flow 674 travels through the pick-up section 670. According to some embodiments, the pick-up section 670 is rotatable (e.g., so that the opening 672 can move between upper -and lower positions in the chamber 660). Moreover, rotation of the pick-up section 670 may vary a rate at which crystals are drawn into the opening 672. For example, when the opening 672 is in an upper position (e.g., pointing toward the gravity drain 650) more crystals may be drawn into the opening 672 as compared to when it is in a lower position (e.g., pointing away from the gravity drain 650). According to some embodiments, rotating a crystal flow control 160 on the face of a microdermabrasion unit 110 causes the pick-up section 670 to rotate. According to another embodiment, an operator can slide the pick-up 670 section along its axis (e.g., instead of, or in addition to, rotating the pick-up section 670 around the axis) to vary that rate at which crystals are drawn into the opening 672 (e.g., more crystals may be drawn into the opening when it is directly under the gravity drain 650).

An agitator 676 (e.g., a thin rod) may be attached to the pick-up section 670. In this case, rotation of the pick-up section 670 may also cause the agitator 676 to move crystals in the chamber 660 (e.g., to dislodge crystals that have become clogged).

Vacuum Air Flows

Figure 7:
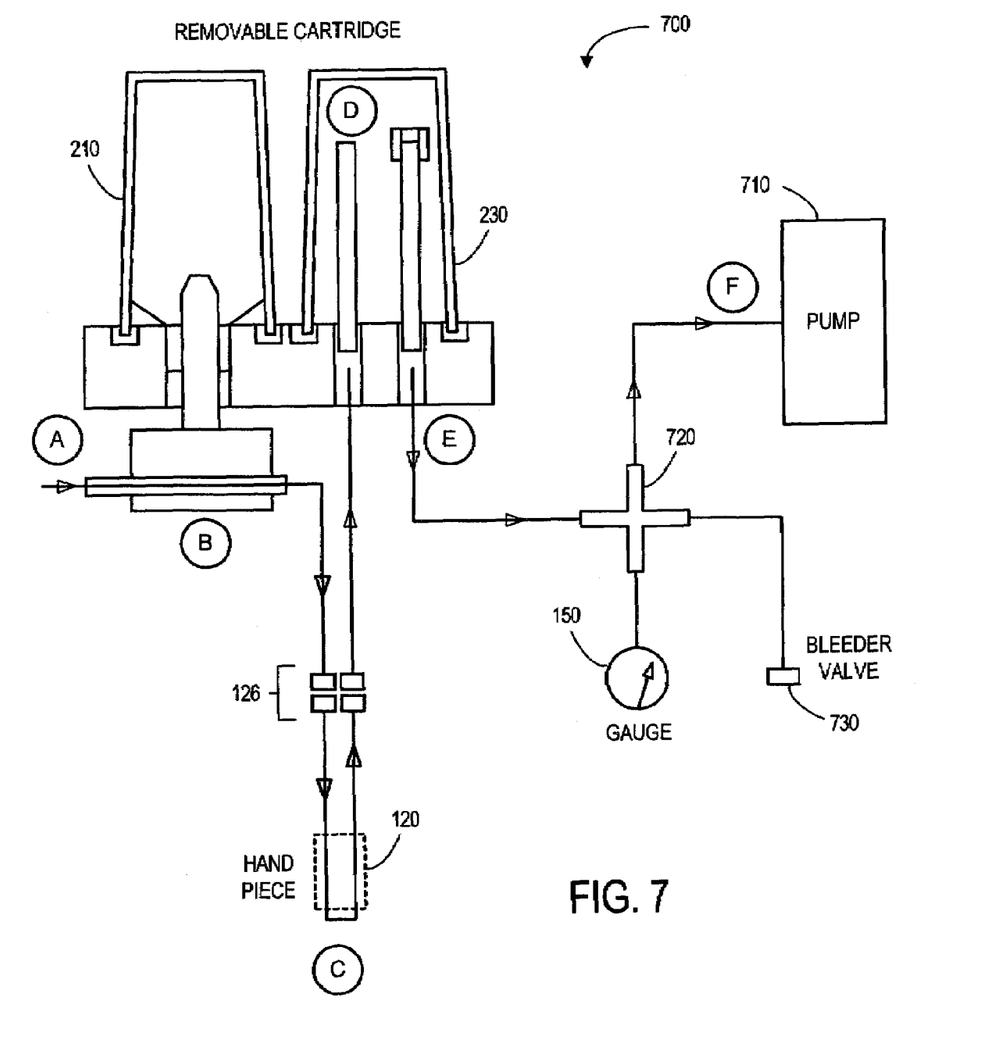
FIG. 7 illustrates a vacuum air flow in a microdermabrasion system according to some embodiments.

FIG. 7 illustrates a vacuum air flow 700 in a microdermabrasion system according to some embodiments. At (A), air is drawn into a pick-up tube located within a microdermabrasion unit. As the air flows through the pick-up tube, crystals in a crystal source portion 210 are supplied to the air flow at (B). The air flow travels through tubing internal to the microdermabrasion unit (e.g., tubing having a ¼" inner diameter and a ⅜" outer diameter) and reaches a set of detachable connectors 126 (e.g., an outflow connector on the face of the microdermabrasion unit). The air flow continues through tubing external to the microdermabrasion unit (e.g., tubing having a 3/16" inner diameter and a 5/16" outer diameter) and eventually reaches a hand-piece 120 where the air flow and the crystals are applied to a patient's skin at (C).

The air flow, used crystals, and skin cells return through tubing to the connectors 126 on the face of the microdermabrasion unit. Internal tubing (e.g., tubing having a ¼" inner diameter and a ⅜" outer diameter) transfers the airflow to a crystal waste portion 230 at (D), and the air flow exits the crystal waste portion at (E). Note that a filter positioned between (D) and (E) may remove the used crystals and skins cells from the air flow (e.g., to protect other elements of the microdermabrasion unit). Finally, the air flow is pulled through tubing and a four-way coupling 720 by a pump 710 at F. The pump 710 may, for example, create a vacuum air flow of 0 to 30 inches of mercury.

According to some embodiments, the four-way coupling 720 is also coupled to a vacuum pressure gauge 150 and/or a bleeder valve 730.

Method

Figure 8:
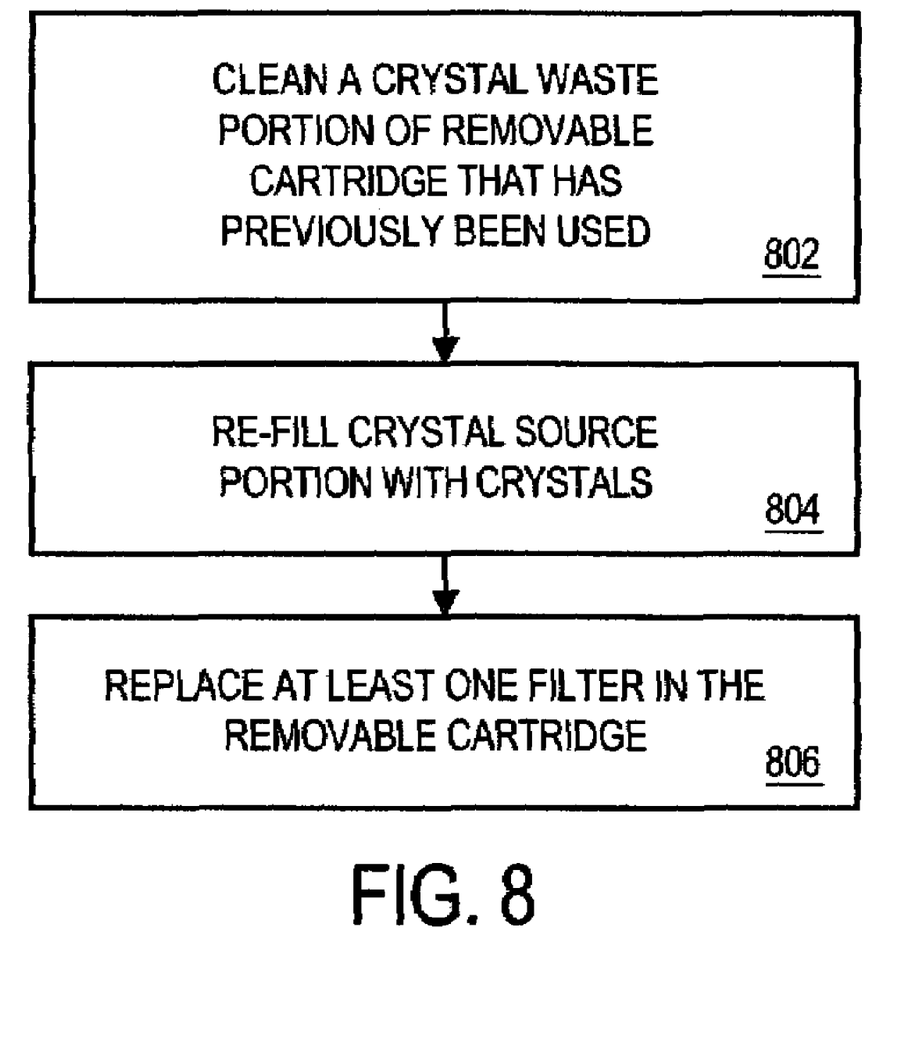
FIG. 8 illustrates a method according to some embodiments.

According to some embodiments, a removable cartridge for a microdermabrasion unit is disposable (e.g., after being used for one patient). FIG. 8 illustrates a method according to other embodiments. Note that the steps illustrated in FIG. 8 may be performed in any order that is practical. The method may be performed, for example, after the crystals in a removable microdermabrasion cartridge have been substantially used (e.g., the crystal supply portion is substantially empty and the crystal waste portion is substantially full). At 802, the crystal waste portion of the removable cartridge is cleaned, and the crystal source portion is re-filled with un-used crystals at 804. At least one filter in the removable cartridge may be replaced at 806 (e.g., because the filter may become less effective after filtering an amount of used crystals and skin cells). In this way, the removable cartridge may be re-used (e.g., for another patient).

Additional Embodiments

The following illustrates various additional embodiments of the present invention. These do not constitute a definition of all possible embodiments, and those skilled in the art will understand that the present invention is applicable to many other embodiments. Further, although the following embodiments are briefly described for clarity, those skilled in the art will understand how to make any changes, if necessary, to the above-described apparatus and methods to accommodate these and other embodiments and applications.

Although certain embodiments have been described, it will be understood by those skilled in the art that a removable cartridge may be configured in any number of ways. For example, a crystal source and/or waste portion might extend into the base (or even be contained entirely within the base). Similarly, a removable cartridge might include crystal source and waste portions without a base (e.g., the crystal source and waste portions might be attached directly to each other). According to another embodiment, the crystal source and waste portions are not attached at all (e.g., they could be separately removable).

The present invention has been described in terms of several embodiments solely for the purpose of illustration. Persons skilled in the art will recognize from this description that the invention is not limited to the embodiments described, but may be practiced with modifications and alterations limited only by the spirit and scope of the appended claims.

What is claimed is:

1. A removable Microdermabrasion unit cartridge, comprising:
   a crystal source portion;
   a crystal waste portion, wherein the removable cartridge is adapted to receive a transfer apparatus from a microdermabrasion unit, the transfer apparatus being adapted to transfer crystals from the crystal source portion to the microdermabrasion unit; and
   a foam unit to prevent crystals from leaving the removable cartridge when the transfer apparatus is not present, wherein the foam unit is to automatically open when the transfer apparatus is inserted into the removable cartridge.

2. The cartridge of claim 1, wherein the transfer apparatus is a pick-up section having a vacuum air flow.

3. The cartridge of claim 1, wherein the foam unit is adapted to permit a flow of air into the crystal source portion.

4. The cartridge of claim 1, wherein the bottom of the crystal source portion (i) includes an opening to receive a transfer apparatus and (ii) inclines from the sides of the crystal source portion down to the opening.

5. The cartridge of claim 1, wherein the crystal waste portion includes:
   a waste input portion to receive used crystals; and
   an air output portion.

6. The cartridge of claim 5, further comprising:
   a filter associated with the air output portion to prevent particles from leaving the crystal waste portion.

7. The cartridge of claim 1, further comprising:
   a base coupled to both the crystal source portion and the crystal waste portion, wherein the base is adapted to be removably coupled to the microdermabrasion unit.

8. The cartridge of claim 1, wherein the crystal source portion is adapted to hold a relatively small amount of crystal.

9. A removable Microdermabrasion unit cartridge, comprising:
- a base adapted to be removably coupled to a microdermabrasion unit;
- a crystal source portion coupled to the base and adapted to receive a transfer apparatus from the microdermabrasion unit, the transfer apparatus being adapted to transfer crystals from the crystal source portion to the microdermabrasion unit;
- a foam unit to prevent crystals from leaving the crystal source portion when the transfer apparatus is not present, wherein the foam unit is to automatically open when the transfer apparatus is inserted into the crystal source portion; and
- a crystal waste portion coupled to the base.

10. The cartridge of claim 9, wherein the transfer apparatus is a pick-up section having a vacuum air flow.

11. The cartridge of claim 9, wherein the bottom of the crystal source portion (i) includes an opening to receive the transfer apparatus and (ii) inclines from the sides of the crystal source portion down to the opening.

12. The cartridge of claim 9, wherein the crystal waste portion includes:
- a waste input portion to receive used crystals; and
- an air output portion.

13. The cartridge of claim 12, further comprising:
- a filter associated with the air output portion to prevent particles from leaving the crystal waste portion.

14. The cartridge of claim 9, wherein the crystal source portion is adapted to hold a relatively small amount of crystal.

* * * * *